United States Patent [19]

Renth et al.

[11] Patent Number: 4,546,102
[45] Date of Patent: Oct. 8, 1985

[54] 1-(6,7-DIMETHOXYQUINAZOL-4-YL)SEMICARBAZIDES

[75] Inventors: Ernst-Otto Renth, Ingelheim; Anton Mentrup, Mainz-Kastel; Kurt Schromm, Ingelheim; Werner Traunecker, Münster-Sarmsheim; Richard Reichl, Gau-Algesheim, all of Fed. Rep. of Germany

[73] Assignee: Boehringer Ingelheim KG, Ingelheim am Rhein, Fed. Rep. of Germany

[21] Appl. No.: 546,864

[22] Filed: Oct. 31, 1983

[30] Foreign Application Priority Data

Nov. 2, 1982 [DE] Fed. Rep. of Germany ....... 3240456

[51] Int. Cl.$^4$ .................. A61K 31/505; C07D 239/94
[52] U.S. Cl. .................................... 514/259; 514/235; 544/279; 544/293; 544/119
[58] Field of Search ................ 544/293, 119; 424/251, 424/248.54

[56] References Cited

U.S. PATENT DOCUMENTS 4,341,782  7/1982  Konishi et al. ...................... 544/292

Primary Examiner—Richard L. Raymond
Assistant Examiner—James H. Turnipseed
Attorney, Agent, or Firm—Hammond & Littell, Weissenberger & Dippert

[57]  ABSTRACT

Compounds of the formula

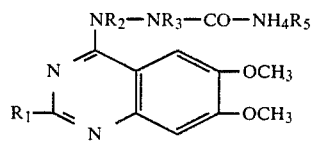

wherein
  $R_1$ is hydrogen, alkyl of 1 to 4 carbon atoms or trifluoromethyl;
  $R_2$, $R_3$ and $R_4$ are each independently hydrogen, methyl or ethyl;
  $R_5$ is hydrogen, alkyl of 1 to 8 carbon atoms, phenyl-(alkyl of 1 to 8 carbon atoms), cycloalkyl of 3 to 7 carbon atoms, (alkoxy of 1 to 4 carbon atoms) carbonyl-methyl, phenyl, substituted phenyl, naphthyl or substituted naphthyl; or
  $R_4$ and $R_5$, together with each other, are alkylene of 4 to 5 carbon atoms, optionally interrupted by —O— or —$NR_6$—, where $R_6$ is alkyl of 1 to 4 carbon atoms;

and non-toxic, pharmacologically acceptable acid addition salts thereof. The compounds as well as their salts are useful as cardiotonics.

6 Claims, No Drawings

1-(6,7-DIMETHOXYQUINAZOL-4-YL)SEMICARBAZIDES

This invention relates to novel semicarbazides and salts thereof, to methods of preparing these compounds, to pharmaceutical compositions containing them as active ingredients, and to a method of using them as cardiotonics.

More particularly, the present invention relates to a novel class of semicarbazides represented by the formula

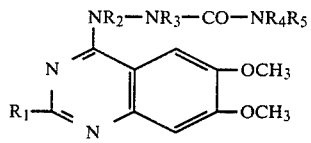
(I)

wherein $R_1$ is hydrogen, alkyl of 1 to 4 carbon atoms or trifluoromethyl;

$R_2$, $R_3$ and $R_4$ are each independently hydrogen, methyl or ethyl;

$R_5$ is hydrogen, alkyl of 1 to 8 carbon atoms, phenyl-(alkyl of 1 to 8 carbon atoms), cycloalkyl of 3 to 7 carbon atoms, (alkoxy of 1 to 4 carbon atoms) carbonyl-methyl, phenyl, substituted phenyl, naphthyl or substituted naphthyl; or $R_4$ and $R_5$, together with each other, are alkylene of 4 to 5 carbon atoms, optionally interrupted by —O— or —$NR_6$—, where $R_6$ is alkyl of 1 to 4 carbon atoms;

and non-toxic, pharmacologically acceptable acid addition salts thereof.

The alkyl moieties in the substituents defined above may be straight or branched.

The preferred alkyl embodiments of $R_1$ are methyl and ethyl.

In the case of $R_5$, the $C_1$-$C_8$-alkyl moiety preferably has 3 to 5 carbon atoms, and the cycloalkyl group has 5 to 6 carbon atoms, while the alkoxy moiety in the alkoxycarbonylmethyl group is preferably methoxy or ethoxy. The substituents in the aromatic groups are, in particular, methyl, ethyl, methoxy, ethoxy, fluorine, chlorine, bromine and $CF_3$. Methyl, methoxy and chlorine should be particularly emphasized. Up to three identical or different substituents may be present. If $R_4$ and $R_5$ represent an alkylene chain optionally interrupted by —O— or —$NR_6$—, they may, for example, represent a group such as —$(CH_2)_4$—, —$(CH_2)_5$—, —$CH_2$—$CH_2$—O—$CH_2$—$CH_2$— or —$CH_2$—$CH_2$—$NCH_3$—$CH_2$—$CH_2$—. The group $R_1$ preferably represents H or $CH_3$. The substituents $R_2$, $R_3$ and $R_4$ preferably represent H.

The compounds embraced by formula I may be prepared by the following methods:

Method A

By reacting a 6,7-dimethoxy-quinazoline of the formula

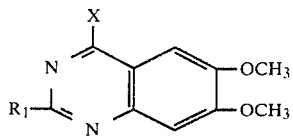
(II)

wherein

X is chlorine or another substituent which can be exchanged for an amino group, and $R_1$ has the meanings previously defined, with a semicarbazide of the formula $$HNR_2-NR_3-CO-NR_4R_5 \quad (III)$$

wherein $R_2$, $R_3$, $R_4$ and $R_5$ have the meanings previously defined, in a solvent which is inert under the reaction conditions.

Suitable solvents include, for example, dimethylformamide, acetonitrile, tetrahydrofuran and alkanols. Depending on the reactivity of the reactants, the reaction is carried out at temperatures between room temperature and the boiling point of the reaction mixture, preferably between 40° and 120° C., in the presence of a basic substance such as sodium carbonate, potassium carbonate or a tertiary amine.

Method B

By reacting a quinazoline of the formula

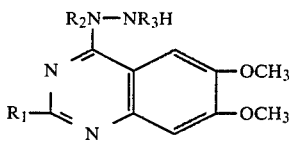
(IV)

wherein $R_1$, $R_2$ and $R_3$ have the meanings previously defined, with an isocyanate of the formula $$OCN-R_5 \quad (V)$$

wherein $R_5$ has the meanings previously defined, in a solvent which is inert under the reaction conditions, to yield a compound of the formula I wherein $R_4$ is hydrogen.

The reaction is carried out in a solvent such as tetrahydrofuran, dioxane, ether, dimethylformamide, toluene, acetone or acetonitrile, preferably at room temperature or while gently heating. The compound of the formula IV may be present in suspension.

Method C

By reacting a compound of the formula IV with a carbamoyl chloride of the formula $$R'_4R'_5-COCl \quad (VI)$$

wherein $R'_4$ and $R'_5$ have the same meanings as $R_4$ and $R_5$, respectively, with the exception of hydrogen, in a solvent which is inert under the reaction conditions. Compounds of the formula I are thus obtained wherein $R_4$ and $R_5$ have the meanings previously defined except hydrogen.

The solvents mentioned in method B, particularly dimethylformamide, are also suitable for use in this method. An acid-binding agent, such as potassium carbonate or sodium carbonate, a tertiary organic base or an excess of the amine, is conveniently used.

Method D

By reacting a compound of the formula IV with a carbamic acid ester of the formula $$R_4R_5N-COOR \quad (VII)$$

wherein $R_4$ and $R_5$ have the meanings previously defined, and R represents an optionally substituted, saturated or unsaturated, aliphatic or araliphatic group, at elevated temperatures in a solvent which is inert under the reaction conditions.

The solvent may be, for example, acetone, dimethylformamide or an alkanol. The reaction temperature is generally between 40° and 80° C. If solvents with a suitable boiling point, such as methanol, are used, the reaction may be carried out at reflux temperature.

Method E

By reacting a compound of the formula (VIII)

wherein $R_1$, $R_2$, $R_3$ and R have the meanings previously defined, with a primary or secondary amine of the formula $$HNR_4R_5 \quad (IX)$$

wherein $R_4$ and $R_5$ have the meanings previously defined, at elevated temperatures in a solvent which is inert under the reaction conditions.

In this process, the solvent and reaction temperatures mentioned in method D may be used.

If salts are obtained as the end products in methods A to E, these may, if desired, be converted into the free bases of the formula I or into salts of other acids. The compounds embraced by formula I are basic substances and therefore form addition salts with inorganic or organic acids. Examples of non-toxic, pharmacologically acceptable acid addition salts are those formed with hydrochloric, hydrobromic, sulfuric, phosphoric, lactic, citric, tartaric, maleic or fumaric acid. The starting compounds are known, or else may be obtained by conventional methods.

The following examples illustrate the present invention and will enable others skilled in the art to understand it more completely. It should be understood, however, that the invention is not limited solely to the particular examples given below.

EXAMPLE 1

1-(6,7-Dimethoxyquinazol-4-yl)-semicarbazide 2.2 g of 6,7-dimethoxy-4-chloro-quinazoline were dissolved in 50 ml of absolute dimethylformamide, 2.2 g of semicarbazide hydrochloride and 5 g of anhydrous potash were added thereto while stirring. The mixture was stirred for 5 hours at 50° C., and the precipitate formed thereby was suction-filtered off, stirred with water, and then recrystallized from dimethylformamide. The crude product was obtained with a 30% yield; m.p. 247°–249° C.

EXAMPLE 2

1-n-Butyl-4-(6,7-dimethoxyquinazol-4-yl)-semicarbazide hydrochloride 3 g of 6,7-dimethoxy-4-chloro-quinazoline were stirred with 3.5 g of 4-n-butyl-semicarbazide in 100 ml of n-amyl alcohol for 2 hours at 100° C. Then, the precipitate which had formed was suction-filtered off, suspended while in hot ethanol and brought to pH 5 by the addition of 2N hydrochloric acid. The clear solution was filtered through charcoal, cooled, suction-filtered and dried in a circulating air drier. The hydrochloride of 4-n-butyl-4-(6,7-dimethoxyquinazol-4-yl)-semi-carbazide, which was obtained with a 70% yield, melted at 216°–217° C. The following compounds were obtained analogously.

1-n-Butyl-4-(6,7-dimethoxy-2-trifluoromethylquinazol-4-yl)-semicarbazide hydrochloride (Mp. 210°–212° C.).

1-n-Butyl-4-(6,7-dimethoxy-2-methylquinazol-4-yl)-semicarbazide hydrochloride (Mp. 295°–297° C.).

The following compounds were also obtained analogously, where

|  | Yield [in % of theory] | Mp. [°C.] |
|---|---|---|
| R—NH—NH—CO—NH—CH$_2$—COOCH$_3$ × HCl | 48 | 214-5 |
| R—NH—NH—CO—NH—CH$_3$ × HCl | 89 | 246-7 |
| R—N(CH$_3$)—NH—CO—NH—n-C$_4$H$_9$ × HCl | 52 | 207-8 |
| R—N(CH$_3$)—N(CH$_3$)—CO—NH—n-C$_4$H$_9$ × HCl | 30 | 203-4 |
| R—NH—NH—CO—NH—C(CH$_3$)$_3$ × HCl | 43 | 296-7 |
| R—NH—NH—CO—NH—C$_6$H$_5$ × HCl | 57 | 199 |
| R—NH—NH—CO—NH—(4-Cl—C$_6$H$_4$) | 59 | 198-199 |
| R—NH—NH—CO—NH—(3-CH$_3$—C$_6$H$_4$) | 55 | 194-95 |

-continued

R = 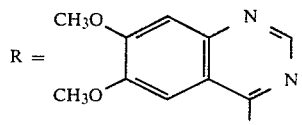

| | Yield [in % of theory] | Mp. [°C.] |
|---|---|---|
| R—NH—N(CH₃)—CO—NH—C₄H₉ | 35 | 210–211 |
| R—NH—NH—CO—N(morpholine) × HCl | 35 | 248–51 |
| R—NH—NH—CO—N—(CH₃)₂ × HCl | 40 | 246–48 |
| R—NH—NH—CO—N(N-methylpiperazine)—CH₃ × HCl | 36 | 287–88 |
| R—NH—NH—CO—N(i-C₃H₇)₂ | 38 | 256–57 |
| R—NH—NH—CO—NH—(CH₂)₅—CH₃ × HCl | 73 | 213–214 |
| R—NH—NH—CO—NH—(CH₂)₄—CH₃ × HCl | 49 | 210–211 |
| R—NH—NH—CO—NH—CH(CH₃)—C₆H₅ × HCl | 53 | 212 |
| R—NH—NH—CO—NH—CH₂—C₆H₅ × HCl | 79 | 210–211 |
| R—NH—NH—CO—NH—CH(CH₃)—C₃H₇ × HCl | 56 | 204 |
| R—NH—NH—CO—NH—CH(C₂H₅)₂ × HCl | 76 | 218–219 |
| R—NH—NH—CO—NH—CH₂—C(CH₃)₃ × HCl | 84 | 208 |
| R—NH—NH—CO—NH—CH(CH₃)—CH(CH₃)₂ × HCl | 77 | 197–199 |
| R—NH—NH—CO—NH—C₂H₅ × HCl | 80 | 226–227 |
| R—NH—NH—CO—NH—CH(CH₃)₂ × HCl | 81 | 220–221 |
| R—NH—NH—CO—NH—(CH₂)₇—CH₃ × HCl | 83 | 208–209 |
| R—NH—NH—CO—NH—cyclohexyl × HCl | 75 | 207–209 |
| R—NH—NH—CO—NH—cyclopentyl × HCl | 82 | 200–201 |
| R—NH—NH—CO—NH—n-C₄H₉ × HCl | 69 | 295–297 |

EXAMPLE 3

1-n-Butyl-4-(6,7-dimethoxyqyinazolin-4-yl)-semicarbazide hydrochloride

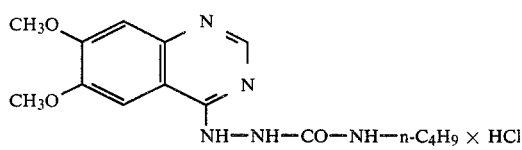

5.12 g of 6,7-Dimethoxy-4-hydrazino-quinazoline were partially dissolved in 200 ml of absolute acetonitrile. Then 5 ml of n-butylisocyanate were added thereto all at once. While the temperature rose slightly, a solution was rapidly obtained. This solution was stirred for 4 hours, and was then allowed to stand overnight. The precipitate formed thereby was suction-filtered off, dissolved in hot ethanol, and mixed with the calculated quantity of ethanolic hydrochloric acid. The hydrochloride of 1-n-butyl-4-(6,7-dimethoxy-quinazolin-4-yl)-semicarbazide crystallized out. After cooling, it was suction-filtered off and dried in a circulating air drier. The end product, which was obtained with a 60% yield, had a melting point of 216°–217° C.

EXAMPLE 4

1-n-Butyl-4-(6,7-dimethoxy-2-methylquinazol-4-yl)-semicarbazide hydrochloride 2.2 of 6,7-dimethoxy-4-hydrazino-2-methyl-quinazoline were suspended in 100 ml of absolute acetonitrile. 2 g of butylisocyanate were added all at once, and the mixture was stirred for 3 hours at room temperature. The base was suction-filtered off, dissolved in ethanol, and then the calculated quantity of ethereal hydrochloric acid was added.

The hydrochloride precipitated thereby (2.3 g, 66% of theory) was suction-filtered off and dried in a drying chamber (Mp. 295°–297° C.).

The 6,7-dimethoxy-4-hydrazino-2-methyl-quinazoline (Mp. 227°–229° C.) needed as the starting compound was obtained by reacting 4-chloro-6,7-dimethoxy-2-methyl-quinazoline with excess hydrazine in dimethylformamide.

Using the same procedure, 1-n-butyl-4-(6,7-dimethoxy-2-trifluoromethylquinazol-4-yl)-semicarbazide hydrochloride (Mp. 210°-212° C.) was also prepared with a 73% yield.

The following compounds were synthesized in analogy to Examples 3 and 4, where R is 6,7-dimethoxyquinazolin-4-yl:

EXAMPLE 5

6,7-Dimethoxy-4-(2-morpholinocarbonyl)-hydrazinoquinazoline hydrochloride 2.2 g of 6,7-Dimethoxy-4-hydrazino-quinazoline were dissolved in 20 ml of dimethylformamide. 2.76 g of anhydrous potash were added, and then 1.7 g of morpholinocarbamic acid chloride were added dropwise thereto, while stirring. The mixture was allowed to react for 2 hours at room temperature, was then poured into ice water, and the precipitate formed thereby was separated by suction filtration. The filter cake was then dissolved in ethanol and converted into the hydrochlo-

|  | Yield [in % of theory] | Mp. [°C.] |
|---|---|---|
| R—NH—NH—CO—NH—CH$_2$—COOCH$_3$ × HCl | 48 | 214-5 |
| R—NH—NH—CO—NH—CH$_3$ × HCl | 89 | 246-7 |
| R—N—NH—CO—NH—C$_4$H$_9$ × HCl<br>\|<br>CH$_3$ | 52 | 207-8 |
| R—N—N—CO—NH—C$_4$H$_9$ × HCl<br>\| \|<br>\| CH$_3$<br>CH$_3$ | 30 | 203-4 |
| R—NH—NH—CO—NH—C(CH$_3$)$_3$ × HCl | 43 | 296-7 |
| R—NH—NH—CO—NH—C$_6$H$_5$ × HCl | 57 | 199 |
| R—NH—NH—CO—NH—(4-Cl—C$_6$H$_4$) | 63 | 198-199 |
| R—NH—NH—CO—NH—(3-CH$_3$—C$_6$H$_4$) | 70 | 194-95 |
| R—NH—N—CO—NH—C$_4$H$_9$<br>\|<br>CH$_3$ | 62 | 210-211 |
| R—NH—NH—CO—NH$_2$ × HCl |  | 247-249 |
| R—NH—NH—CO—NH—C$_2$H$_5$ × HCl | 76 | 226-227 |
| R—NH—NH—CO—NH—CH(CH$_3$)$_2$ × HCl | 87 | 220-221 |
| R—NH—NH—CO—NH—n-C$_5$H$_{11}$ × HCl | 50 | 210-211 |
| R—NH—NH—CO—NH—CH(CH$_3$)—n-C$_3$H$_7$ × HCl | 53 | 204 |
| R—NH—NH—CO—NH—CH(C$_2$H$_5$)$_2$ × HCl | 84 | 218-219 |
| R—NH—NH—CO—NH—CH$_2$—C(CH$_3$)$_3$ × HCl | 80 | 208 |
| R—NH—NH—CO—NH—CH(CH$_3$)—CH(CH$_3$)$_2$ × HCl | 73 | 197-199 |
| R—NH—NH—CO—NH—n-C$_6$H$_{13}$ × HCl | 70 | 213-214 |
| R—NH—NH—CO—NH—n-C$_8$H$_{17}$ × HCl | 80 | 208-209 |
| R—NH—NH—CO—NH—CH$_2$—C$_6$H$_5$ × HCl | 85 | 210-211 |
| R—NH—NH—CO—NH—CH(CH$_3$)—C$_6$H$_5$ × HCl | 59 | 212 |
| R—NH—NH—CO—NH—⟨cyclopentyl H⟩ × HCl | 72 | 200-201 |
| R—NH—NH—CO—NH—⟨cyclohexyl H⟩ × HCl | 70 | 207-209 |
| R—NH—NH—CO—N(CH$_3$)$_2$ × HCl |  | 246-248 |
| R—NH—NH—CO—N(iC$_3$H$_7$)$_2$ × HCl |  | 256-257 |
| R—NH—NH—CO—N(morpholino)O × HCl |  | 248-251 |
| R—NH—NH—CO—N(piperazino)N—CH$_3$ × HCl |  | 287-288 | ride by the addition of ethereal hydrochloric acid. After suction-filtering and drying in a circulating air drier, the hydrochloride of 6,7-dimethoxy-2-(2-morpholinocarbonyl)-hydrazino-quinazoline was obtained with a 40% yield: m.p. 248°-251° C. The following compounds were synthesized in analogy to Example 5, where R is 6,7-dimethoxy-quinazolin-4-yl:

EXAMPLE 6

1-Methyl-4-(6,7-dimethoxyquinazolin-4-yl)-semicarbazide hydrochloride

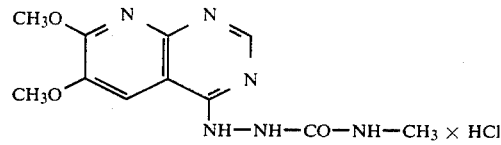

2.2 g of 6,7-dimethoxy-4-hydrazino-quinazoline were suspended in 100 ml of methanol. After the addition of 1.8 g of methyl N-methylcarbamate, the mixture was refluxed for 4 hours. The resulting clear solution was cooled, the precitate formed thereby was suction-fil-

|  | Yield [in % of theory] | Mp. [°C.] |
|---|---|---|
| R—NH—NH—CO—N(CH₃)₂ | 30 | 246–248 |
| R—NH—NH—CO—N(piperazine)N—CH₃ | 35 | 287–288 |
| R—NH—NH—CO—N—(i-C₃H₇)₂ | 38 | 256–257 |
| R—NH—NH—CO—NH₂ × HCl |  | 247–249 |
| R—NH—NH—CO—NH—C₂H₅ × HCl | 76 | 226–227 |
| R—NH—NH—CO—NH—CH(CH₃)₂ × HCl | 87 | 220–221 |
| R—NH—NH—CO—NH—c-C₄H₉ × HCl |  | 216–217 |
| R—NH—NH—CO—NH—C(CH₃)₃ × HCl |  | 296–297 |
| R—NH—NH—CO—NH—n-C₅H₁₁ × HCl | 50 | 210–211 |
| R—NH—NH—CO—NH—CH(CH₃)—n-C₃H₇ × HCl | 53 | 204 |
| R—NH—NH—CO—NH—CH(C₂H₅)₂ × HCl | 84 | 218–219 |
| R—NH—NH—CO—NH—CH₂—C(CH₃)₃ × HCl | 80 | 208 |
| R—NH—NH—CO—NH—CH(CH₃)—CH(CH₃)₂ × HCl | 73 | 197–199 |
| R—NH—NH—CO—NH—n-C₆H₁₃ × HCl | 70 | 213–214 |
| R—NH—NH—CO—NH—n-C₈H₁₇ × HCl | 80 | 208–209 |
| R—NH—NH—CO—NH—C₆H₅ × HCl |  | 199 |
| R—NH—NH—CO—NH—CH₂—C₆H₅ × HCl | 85 | 210–211 |
| R—NH—NH—CO—NH—CH(CH₃)—C₆H₅ × HCl | 59 | 212 |
| R—NH—NH—CO—NH—(cyclopentyl) × HCl | 72 | 200–201 |
| R—NH—NH—CO—NH—(cyclohexyl) × HCl | 70 | 207–209 |
| R—NH—NH—CO—NH—(3-CH₃—C₆H₄) × HCl |  | 194–195 |
| R—NH—NH—CO—NH—(4-Cl—C₆H₄) × HCl |  | 198–199 |
| R—N(CH₃)—NH—CO—NH—n-C₄H₉ × HCl |  | 207–208 |
| R—NH—N(CH₃)—CO—NH—n-C₄H₉ × HCl |  | 210–211 |
| R—N(CH₃)—N(CH₃)—CO—NH—n-C₄H₉ × HCl |  | 203–204 | tered off, dissolved again in hot methanol, and the solution was mixed with the calculated quantity of ethereal hydrochloric acid. This mixture was cooled, and the precipitate was suction-filtered off and dried in a circulating air dryer. The hydrochloride of 1-methyl-4-(6,7-dimethoxyquinazolin-4-yl)-semicarbazdie was obtained with a 50% yield; m.p. 246°–247° C.

The following compounds were prepared in analogy to Example 6, where

R = 6,7-dimethoxyquinazolin-4-yl (structure shown)

| Compound | Yield [in % of theory] | Mp. [°C.] |
|---|---|---|
| R—NH—NH—CO—NH—CH₂COOCH₃ × HCl | 48 | 214–15 |
| R—N(CH₃)—NH—CO—NH—n-C₄H₉ × HCl | 52 | 207–8 |
| R—N(CH₃)—N(CH₃)—CO—NH—n-C₄H₉ × HCl | 30 | 203–4 |
| R—NH—NH—CO—NH—C(CH₃)₃ × HCl | 43 | 296–7 |
| R—NH—NH—CO—NH—C₆H₅ × HCl | 57 | 199 |
| R—NH—NH—CO—NH—(4-Cl—C₆H₄) | 52 | 198–199 |
| R—NH—NH—CO—NH—(3-CH₃—C₆H₄) | 56 | 194–95 |
| R—NH—N(CH₃)—CO—NH—C₄H₉ | 35 | 210–211 |
| R—NH—NH—CO—N(morpholino) × HCl | 22 | 248–51 |
| R—NH—NH—CO—N(CH₃)₂ × HCl | 28 | 246–48 |
| R—NH—NH—CO—N(4-methylpiperazino) × HCl | 35 | 287–88 |
| R—NH—NH—CO—N(i-C₃H₇)₂ | 36 | 256–57 |
| R—NH—NH—CO—NH₂ × HCl | | 247–249 |
| R—NH—NH—CO—NH—C₂H₅ × HCl | | 226–227 |
| R—NH—NH—CO—NH—CH(CH₃)₂ × HCl | | 220–221 |
| R—NH—NH—CO—NH—n-C₄H₉ × HCl | | 216–217 |
| R—NH—NH—CO—NH—n-C₅H₁₁ × HCl | | 210–211 |
| R—NH—NH—CO—NH—CH(CH₃)—C₃H₇ × HCl | | 204 |
| R—NH—NH—CO—NH—CH(C₂H₅)₂ × HCl | | 218–219 |
| R—NH—NH—CO—NH—CH₂—C(CH₃)₃ × HCl | | 208 |
| R—NH—NH—CO—NH—CH(CH₃)—CH(CH₃)₂ × HCl | | 197–199 |
| R—NH—NH—CO—NH—c-C₆H₁₃ × HCl | | 213–214 |
| R—NH—NH—CO—NH—n-C₈H₁₇ × HCl | | 208–209 |
| R—NH—NH—CO—NH—CH₂—COOCH₃ × HCl | | 214–215 |
| R—NH—NH—CO—NH—CH₂—C₆H₅ × HCl | | 210–211 |
| R—NH—NH—CO—NH—CH(CH₃)—C₆H₅ × HCl | | 212 |
| R—NH—NH—CO—NH—(cyclopentyl) | | 200–201 |
| R—NH—NH—CO—NH—(cyclohexyl) | | 207–209 |

In addition, the following compounds were prepared analogously:

1-n-Butyl-4-(6,7-dimethoxy-2-trifluoromethylquinazol-4-yl)-semicarbazide hydrochloride (Mp. 210°–212° C.).

1-n-Butyl-4-(6,7-dimethoxy-2-methylquinazol-4-yl)-semicarbazide hydrochloride (Mp. 295°-297° C.).

EXAMPLE 7

1-Methyl-4-(6,7-dimethoxyquinazolin-4-yl-semicarbazide hydrochloride 1.5 g of 6,7-dimethoxy-4-(2-carbethoxy)-hydrazino-quinazoline, which was obtained by reacting 6,7-dimethoxy-4-hydrazino-quinazoline with ethyl chlorocarbonate, were dissolved in 30 ml of dioxane. After the addition of 2 ml of a 40% methylamine solution, the mixture was heated at 60° C. for 3 hours. The precipitated crystals were suctionfiltered off, suspended in hot ethanol, then the calculated quantity of ethanolic hydrochloric acid was added. A solution was rapidly obtained, which was cooled, suctionfiltered, and the filte cake was dried. The hydrochloride of 1-methyl-4-(6,7 dimethoxyquinazolin-4-yl)-semicarbazide (Mp. 246°-7 C.) was obtained with a 20% yield.

The following compounds were prepared analo gously:

1-n-Butyl-4-(6,7-dimethoxy-2-trifluoromethylquinazol-4-yl)-semicarbazide hydrochloride (Mp. 210°-212 C.).

1-n-Butyl-4-(6,7-dimethoxy-2-methylquinazol-4-yl)-semicarbazide hydrochloride (Mp. 295°-297° C.).

The following were also prepared in analogy to Ex ample 7, where

R = 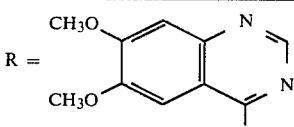

| | Yield [in % of theory] | Mp. [°C.] |
|---|---|---|
| R—NH—NH—CO—NH—CH$_2$—COOCH$_3$ × HCl | 48 | 214-5 |
| R—N(CH$_3$)—NH—CO—NH—n-C$_4$H$_9$ × HCl | 52 | 207-8 |
| R—N(CH$_3$)—N(CH$_3$)—CO—NH—n-C$_4$H$_9$ × HCl | 30 | 203-4 |
| R—NH—NH—CO—NH—C(CH$_3$)$_3$ × HCl | 43 | 206-7 |
| R—NH—NH—CO—NH—C$_6$H$_5$ × HCl | 57 | 199 |
| R—NH—NH—CO—NH—(4-Cl—C$_6$H$_4$) | 52 | 198-99 |
| R—NH—NH—CO—NH—(3-CH$_3$—C$_6$H$_4$) | 46 | 194-95 |
| R—NH—N(CH$_3$)—CO—NH—C$_4$H$_9$ | 42 | 210-11 |
|  | 35 | 248-51 |
| R—NH—NH—CO—N(CH$_3$)$_2$ × HCl | 30 | 246-48 |
|  | 28 | 287-88 |
| R—NH—NH—CO—N(i-C$_3$H$_7$)$_2$ | 35 | 256-57 |
| R—NH—NH—CO—NH$_2$ × HCl | | 247-249 |
| R—NH—NH—CO—NH—C$_2$H$_5$ × HCl | 76° | 226-227 |
| R—NH—NH—CO—NH—CH(CH$_3$)$_2$ × HCl | 87 | 220-221 |
| R—NH—NH—CO—NH—n-C$_4$H$_9$ × HCl | | 216-217 |
| R—NH—NH—CO—NH—n-C$_5$H$_{11}$ × HCl | 50 | 210-211 |
| R—NH—NH—CO—NH—CH(CH$_3$)—n-C$_3$H$_7$ × HCl | 53 | 204 |
| R—NH—NH—CO—NH—CH(C$_2$H$_5$)$_2$ × HCl | 84 | 218-219 |
| R—NH—NH—CO—NH—CH$_2$—C(CH$_3$)$_3$ × HCl | 80 | 208 |
| R—NH—NH—CO—NH—CH(CH$_3$)—CH(CH$_3$)$_2$ × HCl | 73 | 197-199 |
| R—NH—NH—CO—NH—n-C$_6$H$_{13}$ × HCl | 70 | 213-214 |
| R—NH—NH—CO—NH—n-C$_8$H$_{17}$ × HCl | 80 | 208-209 |
| R—NH—NH—CO—NH—CH$_2$—C$_6$H$_5$ × HCl | 85 | 210-211 |
| R—NH—NH—CO—NH—CH(CH$_3$)—C$_6$H$_5$ × HCl | 59 | 212 |
| 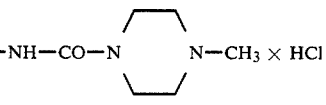 | 72 | 200-201 |

| | Yield [in % of theory] | Mp. [°C.] |
|---|---|---|
| R—NH—NH—CO—NH—⟨H⟩ × HCl where R = 6,7-dimethoxyquinazolinyl | 70 | 207–209 |

The compounds of the present invention, that is, those embraced by formula I above and non-toxic, pharmacologically acceptable acid addition salts thereof, have useful pharmacodynamic properties. More particularly, they exhibit longlasting phosphodiesterase-inhibiting and heart-stimulating activities in warm-blooded animals. They increase the contractile force of the heart muscle without significantly affecting the heart rate.

This selectivity, in particular, makes them useful for the therapeutic and prophylactic treatment of pathological heart conditions, particularly heart failure. Apart from their effect on heart muscle, the compounds according to the invention also have vasodilating and hypotensive properties, and in some cases they increase the circulation of blood through the kidneys and broncholysis. The therapeutic and prophylactic dose depends on the nature and gravity of the disorder and on the route of administration.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds according to the present invention for oral administration is from 20 to 1000 mg per day, administered in 2 to 4 separate doses, and the effective amount for parenteral administration is 1 to 300 mg.

The following examples illustrate a few pharmaceutical compositions comprising a compound of the present invention as an active ingredient and represent the best modes contemplated of using the invention. The parts are parts by weight.

EXAMPLE 8

Tablets

The tablet composition is compounded from the following ingredients:

| | |
|---|---|
| 1-(6,7-dimethoxyquinazol-4-yl)-semicarbazide | 100 parts |
| Colloidal silicic acid | 10 parts |
| Lactose | 118 parts |
| Potato starch | 60 parts |
| Polyvinylpyrrolidone | 6 parts |
| Sodium cellulose glycolate | 4 parts |
| Magnesium stearate | 2 parts |
| TOTAL | 300 parts |

Preparation:

The ingredients are processed in the usual way to form 300 mg-tablets each of which contains 100 mg of the active ingredient.

EXAMPLE 9

Capsules

The capsule filler composition is compounded from the following ingredients:

| | |
|---|---|
| 1-(6,7-dimethoxyquinazol-4-yl)-semicarbazide | 200 parts |
| Corn starch | 200 parts |
| TOTAL | 400 parts |

Preparation:

The ingredients are intimately admixed with each other, and 400 mg-portions of the mixture are filled into gelatin capsules of suitable size. Each capsule contains 200 mg of the active ingredient.

Any one of the other compounds embraced by formula I or a non-toxic, pharmacologically acceptable acid addition salt thereof may be substituted for the particular active ingredient in Examples 8 and 9. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

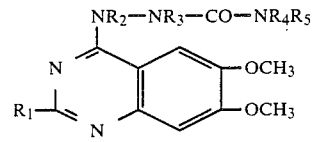

wherein $R_1$ is hydrogen, alkyl of 1 to 4 carbon atoms or trifluoromethyl;

$R_2$, $R_3$ and $R_4$ are each independently hydrogen, methyl or ethyl;

$R_5$ is hydrogen; alkyl of 1 to 8 carbon atoms; phenyl-(alkyl of 1 to 8 carbon atoms); cycloalkyl of 3 to 7 carbon atoms; (alkoxy of 1 to 4 carbon atoms) carbonyl methyl; phenyl; phenyl substituted by one to three identical or different substituents selected from the group consisting of methyl, ethyl, methoxy, ethoxy, fluorine, chlorine, bromine and $CF_3$; naphthyl or naphthyl substituted by one to three identical or different substituents selected from the group consisting of methyl, ethyl, methoxy, ethoxy, fluorine, chlorine, bromine and $CF_3$; and $R_4$ and $R_5$, together with each other, are alkylene of 4 to 5 carbon atoms optionally interrupted by —O— or —$NR_6$—, where $R_6$ is alkyl of 1 to 4 carbon atoms; or a non-toxic, pharmacologically acceptable acid addition salt thereof.

2. A compound of claim 1, where $R_1$ is hydrogen or methyl, $R_2$, $R_3$ and $R_4$ are hydrogen; and $R_5$ is hydrogen, alkyl of 3 to 5 carbon atoms; cycloalkyl of 5 to 6 carbon atoms, (alkoxy of 1 to 2 carbon atoms) carbonyl-methyl, phenyl, chlorophenyl, α-naphthyl, β-naphthyl or benzyl; or $R_4$ and $R_5$, together with each other, are —$CH_2$—$CH_2$—O—$CH_2$—$CH_2$— or
—$CH_2$—$CH_2$—$NCH_3$—$CH_2$—$CH_2$;

or a non-toxic, pharmacologically acceptable acid addition salt thereof.

3. A compound of claim 1, which is 1-[6,7-dimethoxyquinazol-4-yl]-simicarbazide or a non-toxic, pharmacologically acceptable acid addition salt thereof.

4. A compound of claim 1, which is 1-n-butyl-4-(6,7-dimethoxyquinazol-4-yl)-simicarbazide or a non-toxic, pharmacologically acceptable acid addition salt thereof.

5. A cardiotonic pharmaceutical composition consisting essentially of an inert pharmaceutical carrier and an effective cardiotonic amount of a compound of claim 1.

6. The method of increasing the cardiac output of a warm-blooded animal in need thereof, which comprises perorally or parenterally administering to said animal an effective cardiotonic amount of a compound of claim 1.

* * * * *